United States Patent [19]

Tan et al.

[11] Patent Number: 5,069,147
[45] Date of Patent: Dec. 3, 1991

[54] TOURING SYSTEM FOR A WASTE PROCESSING PLANT

[76] Inventors: Palatan L. J. Tan, 2 Fl., No. 23, Syh Chuan Rd., Taichung, Taiwan; David Tan; Richard Tan, both of 34-25 150 Place #3B, Flushing, N.Y. 11354

[21] Appl. No.: 519,516

[22] Filed: May 3, 1990

[51] Int. Cl.⁵ .............................................. F23B 7/00
[52] U.S. Cl. ..................................... 110/349; 110/235
[58] Field of Search ............... 110/235, 246, 193, 349; 122/1 R; 52/79.7

[56] References Cited

U.S. PATENT DOCUMENTS 4,944,236 7/1990 Sheen .............................. 110/235 X Primary Examiner—Edward G. Favors
Attorney, Agent, or Firm—Browdy and Neimark

[57] ABSTRACT

A touring system is provided on a waste processing plant which includes a number of processing stations, including reception, sorting, mixing na pumping, fermentation, pressing, and refining. A housing is provided on each station. A passage is connected between every two adjacent housings. A transparent dome is provided in each housing so that people in the housing may observe a processing or a treatment of the waste without feel disgust and may realize how the waste is reusable.

5 Claims, 5 Drawing Sheets

TOURING SYSTEM FOR A WASTE PROCESSING PLANT

BACKGROUND OF THE INVENTION

The present invention relates to a touring system, and more particularly to a touring system for a waste processing plant.

The treatment of waste, garbage and trash has become a serious problem, and has become one of the most important things first needed to be dealt with today. A dump or a dumping ground is still in use today for collecting waste and trash. The waste and trash, including tires, plastic materials, organic materials, ferrous metal, combustibles, . . . etc., of some dumping ground is burned on the ground or in a combustion furnace, which may produce poisonous gases and may pollute our atmosphere. The waste of other dumping ground is buried into the ground, which may pollute the water supply nearby and may produce disgusting odor. In addition, the waste, such as tire, glass, ferrous metal or plastic material, is still there after a decade, a century or may be longer, and will not disappear automatically. Accordingly, the impression of the waste to people is disgustful.

In addition, it has become harder and harder to find a space to dump waste in most of the countries, especially the industrialized countries. People create garbage and demand that the government must take care of their garbage. However, no one wants a garbage treating plant in their neighborhood because of health concerns and devaluation of their real estate. It is impossible for the government to locate a treatment site that is not next to some private land.

A waste processing plant has been developed to treat the waste in an environmentally favorable manner. The waste which is collected in the plant is sorted and classified into several categories, such as plastic materials, combustibles, organic materials, ferrous metals, glass and other heavy inert materials. The plant comprises a plurality of processing stations for treating the sorted waste, such as a station for collecting plastic materials, a fermentation station for treating the organic material, a refining station for treating the organic materials from the fermentation station, a station for treating gas which is produced in the fermentation station, a combustion furnace for combusting the combustibles and for melting metal materials, . . . etc., so that all the waste is useful or reusable. However, the processing stations are generally enclosed or buried underground so that no body can see the treatment processes and people do not know how the waste is useful and reusable.

The present invention has arisen to mitigate and/or obviate the afore-described disadvantages of the conventional waste processing plant, which is generally viewed in the public's eye as a polluting source and hence the strong opposition by nearby residents to the locating and constructing of new waste treatment plants.

SUMMARY OF THE INVENTION

The primary objective of the present invention is to provide a touring system for a waste processing plant which provides a plurality of show rooms or the like for observing or watching the treatment processes of the waste in order to remove the disgusting impression of the waste from people.

In accordance with one aspect of the invention, there is provided a touring system for a waste processing plant which comprises a number of processing stations, including a reception station, a sorting station, a mixing and pumping station, a fermentation station, a pressing station, and a refining station. The touring system has a housing provided on each station. A transparent dome is provided in an opening which is formed in a floor of each housing. The housing is separated from the processing station by the floor and the transparent dome. A passage is connected between every two adjacent housings so that visitors may have access to different housings. Inside each housing is a transparent dome that clearly shows a view of the waste processing station below. An approach which is enclosed is connected to the reception station. People may observe a processing or a treatment of the waste without feel disgusting.

Further objectives and advantages of the present invention will become apparent from a careful reading of the detailed description provided hereinbelow, with appropriate reference to the accompanying drawings.

DETAILED DESCRIPTION OF THE INVENTION

Figure 1:
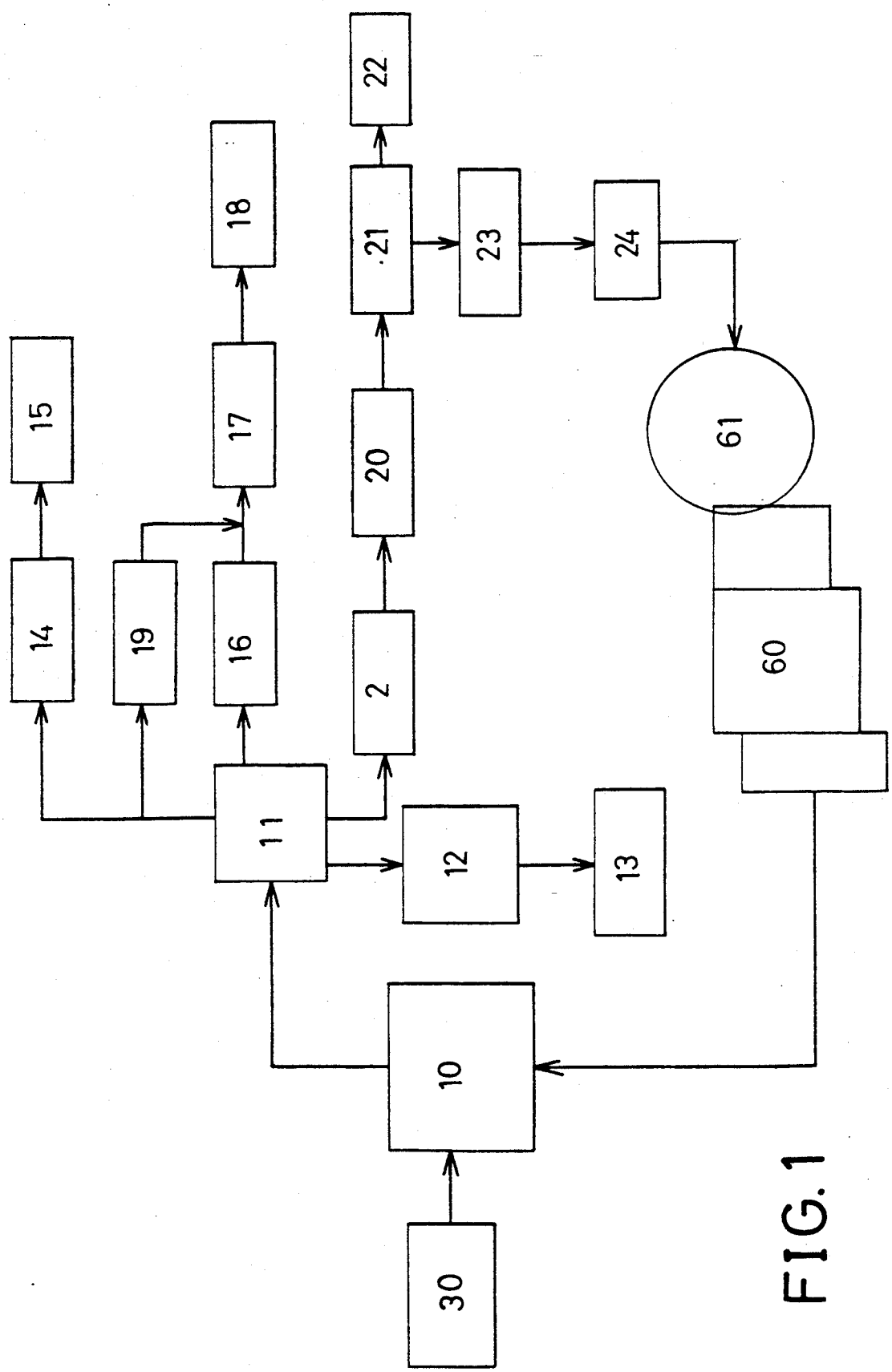
FIG. 1 is a block diagram illustrating the processing stations of the waste processing plant.
Figure 2:
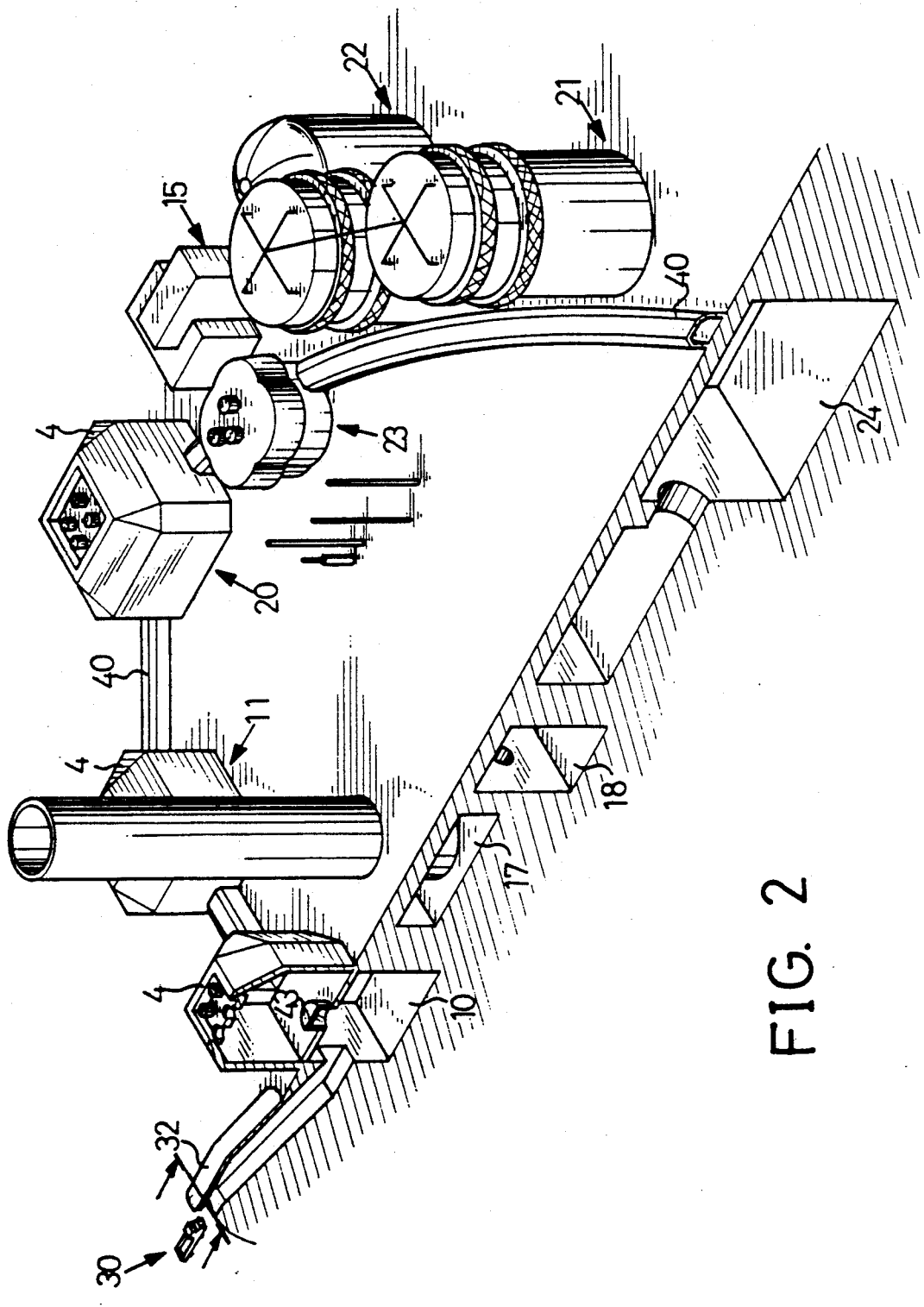
FIG. 2 is a partial cross sectional view of the waste processing plant.

Referring to the drawings and initially to FIGS. 1 and 2, the touring system in accordance with the present invention is provided for a waste processing plant which comprising a plurality of processing stations. As shown in FIG. 1, the waste processing plant has a reception station 10 for receiving and storing waste, a vacuum is preferably provided in the reception station 10 for removing the flavor or odor of the waste. A sorting station 11 is provided for sorting and separating the waste into several kinds of waste, such as combustibles 16, organic materials 2, plastic and rubber materials 12, metal 19 and glass 14. A crushing station 15 is provided for crushing the glass 14. A combustion station 17 is provided for combusting the combustibles, the metal can be melted in the combustion station 17. A heat recovery station 18 is provided for changing the heat energy generated from the combustion station 17 to other useful energy, such as electrical energy. A working station 13 is provided for treating the plastic and rubber materials 12. A mixing and pumping station 20 is provided for transforming the organic materials into pasty slurry which is good for fermentation. A fermentation station 21, the pasty slurry produced in the mixing and pumping station 20 is digested by bacterial populations. A treatment station 22 is provided for treating the gas which is produced in fermentation station 21, the gas is decarbonated, desulphurized, dehydrated and compressed. A pressing station 23 is provided for pressing the material resulting from digestion so that excess liquid is separated therefrom, the liquid is returned to the mixing and pumping station 20. A refining station 24 is provided for refining the material from the pressing station 23 so that a final organic ameliorator which is high yield fertilizer is formed.

Figure 3:
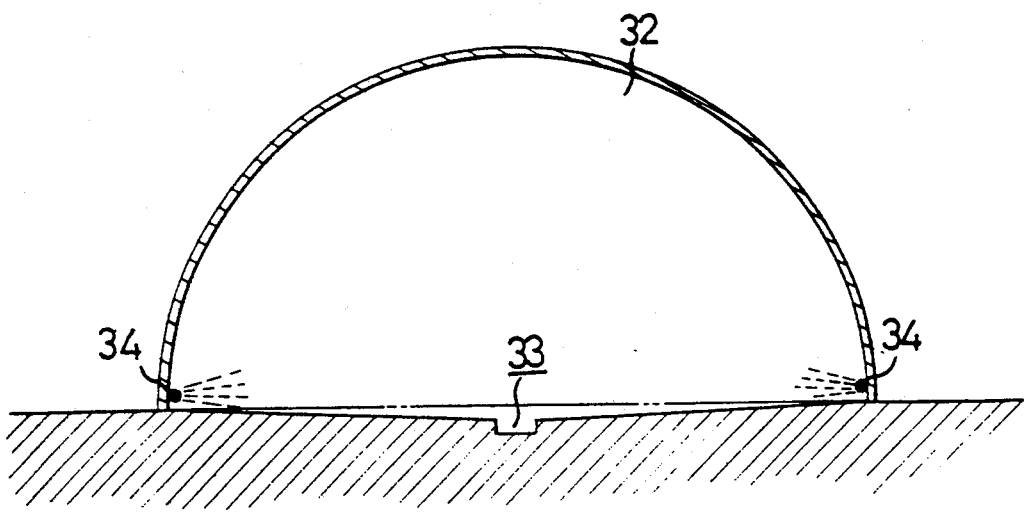
FIG. 3 is a cross sectional view of an entrance of the waste processing plant, taken along lines 3—3 of FIG. 2.
Figure 4:
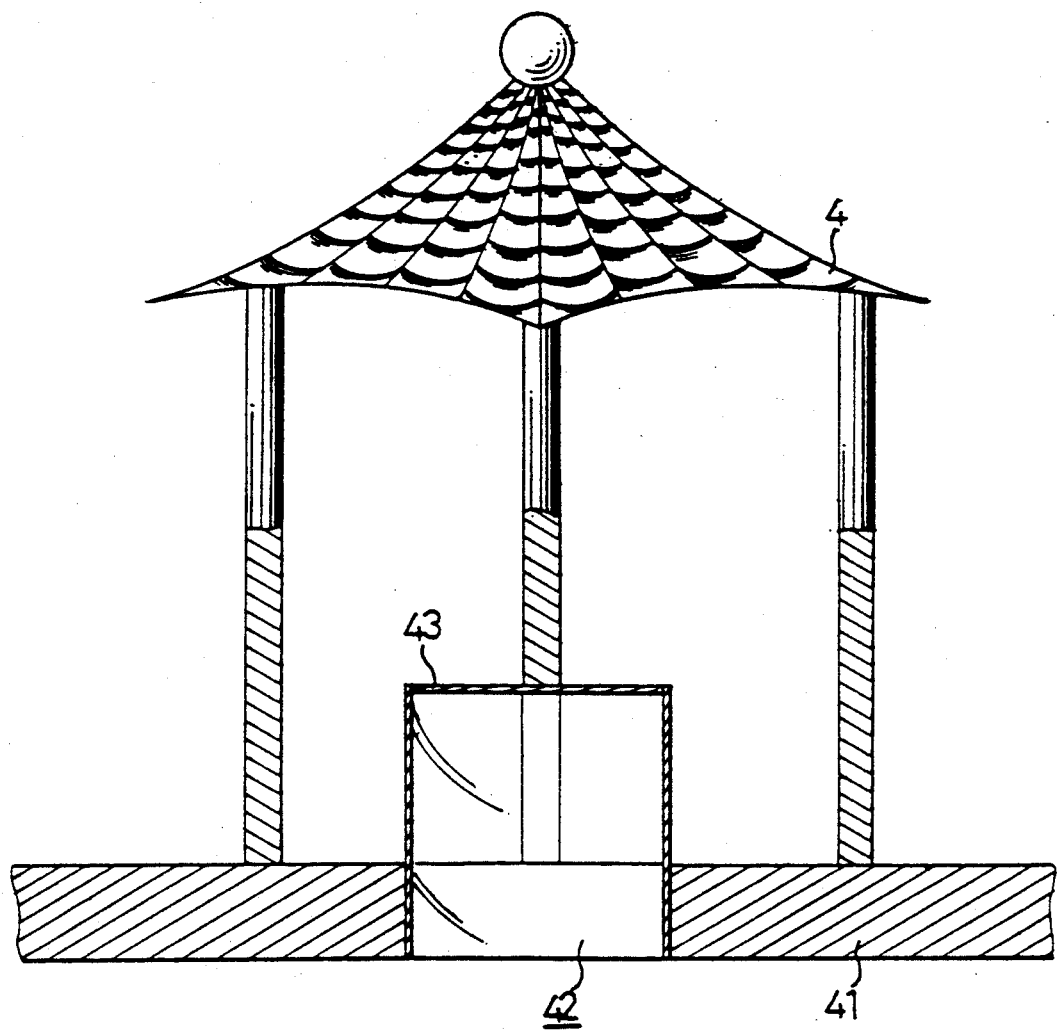
FIG. 4 is a schematic view illustrating a show room.

Referring next to FIGS. 2, 3 and 4, the truck 30 which carries waste enters an approach 32 which is preferably enclosed and preferably has a long distance away from the waste processing plant area so that the odor of the waste will not dissipate and spread to the tourist sections. As shown in FIG. 3, the floor of the approach 32 is tapered toward a center thereof, a groove 33 is longitudinally formed along the center of the approach 32. A sprinkler pipe 34 is provided on each side of the approach 32 for sprinkling water to the floor of the approach 32 in order to clean the dirt or liquid dropped from the truck 30. The water is collected and is supplied into the mixing and pumping station 20. The actual waste processing takes place below ground level, partitioned into different stations as described above. A housing 4 is substantially provided on top of each station, except the combustion station 17. A passage 40 which is preferably transparent provides tourist access between the housings 4. As shown in FIG. 4, a transparent dome 43 includes a transparent sheet disposed on an upper end of a transparent tube which protrudes from an opening 42 which is preferably formed in a center of the floor 41 of each housing 4 so that visitors in the housing 4 can clearly view the treatment or processing of each station. The lower end of the transparent tube of the dome 43 extends in the opening 42 and is closely fixed to the floor 41. It is preferable that a seal is provided between the floor 41 and the transparent dome 43 so that the odor of the processing station thereunder will not dissipate and spread to the housings 4. Each housing 4 will have an audio/visual aids to explain to the visitors what stage of processing he will observe in this station, and other pertinent facts about the particular station below. As shown in FIG. 2, the processing stations of the waste processing plant are disposed under ground so that visitors can see these processing stations only in the housings 4 by viewing through the dome 43.

Referring again to FIG. 1, in addition to the housings 4, an administrative house 60 and a show room 61 are provided. Visitors may enter the touring system from the administrative house 60. The show room 61 may exhibit the flow chart of the waste processing plant and may exhibit the environmental protection information of yesterday, today or the future. The environment around the touring system can be decorated as a garden where also can be provided with fruit trees. The final organic ameliorator which is high yield fertilizer can be used as the nutriment for the plants in the garden. This demonstrates to the visitors that the processed waste can be very useful and dispel their previously very negative impression of municipal solid waste as a dirty, unhealthy and disgusting garbage problem without a solution. In addition, amusement facilities can be disposed in the touring system for providing amusement for the visitors.

Figure 5:
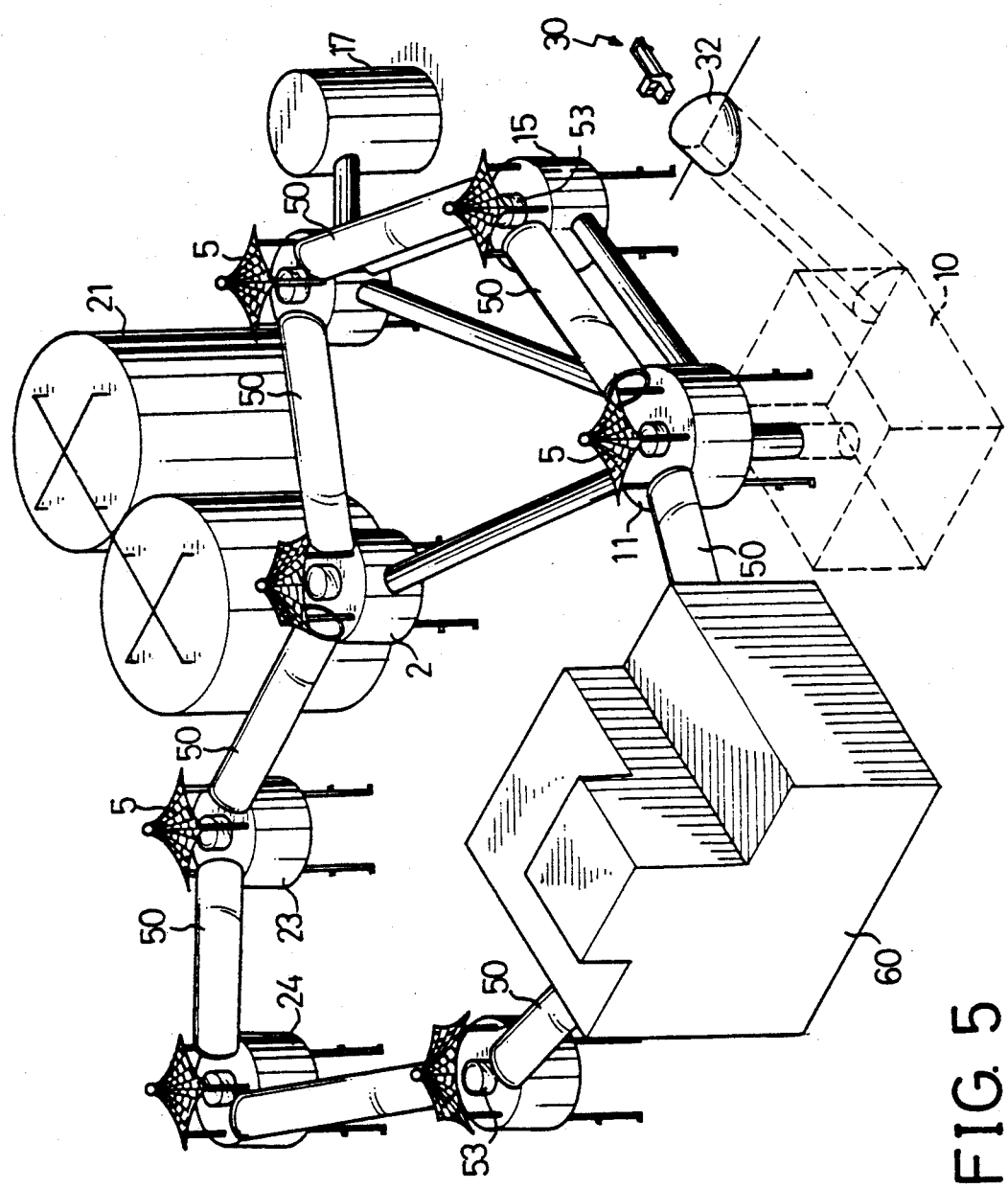
FIG. 5 is a schematic view illustrating another embodiment of the waste processing plant.

Referring next to FIG. 5, illustrated is another embodiment in accordance with the present invention. In this embodiment, the processing stations 11, 15, 2, 23, 24. . . etc., are elevated except the reception station 10. A housing 5 which is open is provided upon each processing station and a passage 50 is connected between the housings 5. The visitors will again be allowed to tour the plant by observing through a transparent dome 53 to see the processing stations below. By elevating the processing stations and housings above ground, much more space is obtained and can be used for other purposes, such as exhibition, parking or the like. In addition, visitors can have a clearer view of the ground.

Alternatively, in accordance with another embodiment of the invention, the touring system can be built at ground level and will be a net work of transparent tunnels that run through the entire plant. The network of tunnels will sometimes follow the side of the factory walls and other times the floor of the factory and still other times follow the ceiling. Since the tunnels run through the factory, the visitors can get closer to the processing stations and clearly see how the waste is processed.

Accordingly, the touring system in accordance with the present invention has a clean and pleasant environment so that people may observe and watch the processing treatment of the waste and will not feel disgust. In addition, people may realize how the waste can be reused. This has high educational values and allows the public to accept and embraces the locating of such a waste processing touring system in their neighborhood.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A touring system for a waste processing plant, said waste processing plant comprising a plurality of processing stations, including a reception station; said touring system comprising a housing provided upon each said station, a transparent device being provided in an opening which is formed in a floor of each said housing, said housing being separated from said processing station by said floor and said transparent device; a passage being connected between every two adjacent housings; an approach which is substantially enclosed being connected to said reception station; and people may observe a processing or a treatment of a waste in said housing without feeling disgus, and may realize how said waste is reusable.

2. A touring system according to claim 1, wherein a floor of said approach is tapered toward a center thereof, a groove is longitudinally formed along said center of said approach; and a sprinkler pipe is provided on each side of said approach for sprinkling water to wash said floor.

3. A touring system according to claim 1, wherein said transparent device is a transparent dome including a transparent sheet disposed upon a transparent tube, said transparent tube is protruded from said opening and is closely fixed to said floor of said housing so that people can see said processing of said waste via said tranparent dome.

4. A touring system according to claim 1, wherein said processing stations are disposed underground so that people can not see any of said processing stations on the ground.

5. A touring system according to claim 1, wherein said processing stations are elevated, said housings are further provided upon said processing stations so that people can have a clearer view of the ground.

* * * * *